US00PP09072P

United States Patent [19]

Felker

[11] Patent Number: Plant 9,072

[45] Date of Patent: Mar. 14, 1995

[54] SOUTH AMERICAN MESQUITE 'LAURIE'

[75] Inventor: Peter Felker, R.R. 1 Box 525u, Kingsville, Tex. 78363

[73] Assignee: Peter Felker, Kingsville, Tex.

[21] Appl. No.: 126,990

[22] Filed: Sep. 27, 1993

[51] Int. Cl.[6] ..... A01H 5/00

[52] U.S. Cl. ..... Plt./51.1

[58] Field of Search ..... Plt. 51.1

[56] References Cited

PUBLICATIONS

Huxley, A., et al., "Prosopis" *The New Royal Horticultural Society Dictionary of Gardening,* vol. 3, 1992, Stockton Press, N.Y., pp. 726 and 727.

Felker, P., "Mesquite" New Agricultural Crops, 1979, Westview Press, Boulder, Colo., pp. 89–132.

*Primary Examiner*—James R. Feyrer

*Attorney, Agent, or Firm*—Daniel Vera

[57] ABSTRACT

A new and distinct variety of South American Mesquite having the following unique combination of desirable features:

1. Thornless nature.
2. Cold hardy to 10 F.
3. Slower vertical growth, with a greater girth to height ratio, than other South American Mesquites that leads to a tree with less of a tendency to lean with the wind.
4. Yellow pods about 12 cm long containing about 30% sugar which are useful for animal feed.
5. Feathery leaves, commonly containing 4 pair of pinnae.
6. Good resistance to stem fungal pathogens *Lasiodiplodia theobromae* and *Pestalotiopsis guepinii.*
7. Complete resistance to cotton root rot, *Phymatotrichum omnivorum.*

4 Drawing Sheets

ORIGIN OF THE VARIETY

The present invention relates to a new and distinct variety of South American ornamental "mesquite" known botanically as *Prosopis alba* that has been designated *Prosopis alba* 0591 row 2 tree 1 and row two tree 11. The new variety will be named Laurie. I discovered the new variety in an experimental field trial at Texas A&M University Kingsville in 1990 as part of a long term genetic improvement process. The source of the original germplasm leading to this plant was obtained from Texas A&M University-Kingsville germplasm collections, and was properly released to me through the Texas A&M University System Office.

The genetic background of *Prosopis alba* 0591 row 2 tree 1 and row two tree eleven is as follows. In January 1972, Dr. Beryl Simpson, now Botany Department Head at the University of Texas at Austin, collected seed from a single 8 m tall *Prosopis alba* tree on a trip from Santiago del Estero to Chero, Argentina that she designated #4272. Our accession number for this seedlot was 0039. I obtained some of this seed which was used to establish a field trial with 55 types of Prosopis and other tree legumes in the California Imperial Valley in April 1979. Three thorny, cold-hardy *Prosopis velutina* families from Arizona were the only accessions in this trial that had pubescens on the young stems and leaves. Due to lack of thorns, erect form and rapid growth, seed from an individual tree of accession 0039, designated Block 14 Variety 11 (B14V11) in the California Imperial Valley field trial, was collected. Seed from B14V11 was designated 0591 (0039). I assisted in the planting of one hundred trees of 0591(0039) on the Texas A&M Kingsville field station in April of 1981. In Christmas 1983, 100 consecutive hr of freezing weather with a minimum of 10 F caused severe damage to many subtropical plants in Texas. In the spring of 1984, I scored over 1000 trees of *Prosopis alba, P. chilensis, P. venutina, P. articulata* and *P. glandulosa* for cold tolerance and lack of thorns. When evaluated in the spring of 1984, tree 1 and tree 11 in row 2 of *Prosopis alba* 0591 were thornless and had 75% of above-ground survival. At Christmas 1989, a similar freeze to that of Christmas 1983 occurred in which temperature were below 20 F. for 20 hr and minimum of 10 F. occurred. In the spring of 1990, the 100 trees of *P. alba* 0591 were again ranked where it was found that row 2 tree 1 had 95% intact canopy and tree 11 had 100% intact canopy.

The significance of the combination of thornlessness and cold hardy characters is most clearly illustrated by using rankings from *Prosopis alba* 0166 growing in Kingsville, Tex. Seed from this accession was derived from an ornamental *Prosopis alba* growing about 15 miles north of the Salton Sea in the California. This is from seedstock typical of the introduced "Chilean Mesquites" widely used as ornamentals in the Tuscon/Phoenix area. After the freeze of 1983, out of a population of 100 trees, 31 thornless trees froze to the ground but only 15 thorny trees froze to the ground. In contrast, 18 thorny trees survived without frost damage but only 6 thornless trees survived without frost damage. In the freeze of 1989, all thornless trees of this accession froze to the ground but numerous thornless trees were not damaged.

It is significant to point out that the thorny, multistemmed trees of *P. alba* 0166 which survived had many characters resembling the cold-hardy, Californian native *P. glandulosa* var. *torreyana* which occurred in close proximity to the parent *P. alba* 0166 tree in the Coachella Valley. Similarly, the thorny cold hardy parents also had some stem cankers, probably caused by *Lasiodiplodia theobromae* and *Pestalotiopsis guepinii* that caused 100% mortality to California native *Prosopis glandulosa* var *torreyana* when grown in Texas. No stem cankers were ever observed on the improved clone reported here.

In 1983, 150 trees of *P. alba* clone B2V50 survived the freeze without damage about 90 miles southwest of Kingsville near Zapata, Tex. Clone B2V50 is a high biomass producing tree that I cloned in 1980 from a field trial in California from progeny of *Prosopis alba* 0194. Seed of *P. alba* 0194 was obtained from a commercial nursery south Parker Dam along the Colorado River during a collection trip in 1978. Clones of B2V50 were shared with university collaborators in Tucson and Phoenix for U.S. Department of Energy field trials in the mid-1980's. Mr. Ron Gass of Mountain State Wholesale near Phoenix, Ariz., trademarked clone B2V50 as the "Colorado" mesquite for sale as an ornamental in Arizona. All unprotected trees of clone B2V50, larger than 10 cm in diameter, froze to the ground in Kingsville as a result of the freeze of Christmas 1989.

Base on a comparison of stem form, and survival from the freeze in both 1983 and 1989, *P. alba* 0591 (0039) row 2 tree 1 and tree 11 were chosen for asexual propagation. No damage occured to Texas native mesquites i.e. *P. glandulosa* var. *glandulosa* during either the 1983 or 1989 freeze.

Since row 2 tree 1 and row 2 tree 11 have the same foliage pattern with 4 pair of bipinnate leaves, each containing about 52 pairs of leaflets, since they are both thornless, and since they had virtually the same cold hardy ranking in 1983 and 1989, there is no phenotypic difference between these trees. Furthermore since they had the same mother and grandmother tree, there is strong genetic evidence to suggest they are of the same genotype. It would not be unusual to expect 2 trees out of a population of 100 progeny from the same mother and grandmother to be identical. Some phenotypic segregation has occurred among the 100 progeny resulting from the 0591 mother tree, but these trees are phenotypically identical. Using every testing method of todays standards there is no difference in these trees and we conclude they are of the same genotype.

In the early 1980's Dr. Stuart Lyda, formerly Plant Pathologist at Texas A&M University, College Station, examined the resistance of *Prosopis alba* to cotton root rot, *Phymatotrichum omnivorum* in greenhouse studies and found it to be completely resistant to this pathogen.

ASEXUAL PROPAGATION OF THE VARIETY

Based on this data 0591(0039) row 2 tree 1 and tree 11 were asexually propagated by air layering in the summer of 1990. The air layers were made on parent trees in the Texas A&M University experimental field trials located one quarter mile northwest of the Kingsville campus. After the air layers were rooted, they were potted into 20 liter containers at the Plantclone Inc greenhouse at the corner of Corral and 14th Street in Kingsville. These repotted air layers were used to make stock plants for rooted cuttings. Mature trees give less than 1% success in rooting cuttings while stock plants derived from air layers yield 70% success in rooting cuttings.

After propagating this clone in the greenhouse from 1990 to 1993, the foliage pattern and lack of thorns has remained constant.

Based on these results, I believe that *Prosopis alba* 0591 "Laurie" represents a new and improved variety of South American mesquite that is both thornless and has greater cold hardiness than other "South American Mesquites."

The height growth of my new variety is less than that of the B2V50 but the ratio of diameter growth to height growth of the new variety is greater than that of clone B2V50. Large trees of clone B2V50 suffer from excessive leaning due to a small stem diameter to height ratio.

BRIEF DESCRIPTION OF THE PHOTOGRAPHS

FIG. 1 is a color photograph of the foliage illustrating lack of thorns.

FIG. 2 is a color photograph of a pod showing the falcate shape and the yellowish color.

FIG. 3 is a color photograph of 7 cm diameter stems showing the reddish brown coloration.

FIG. 4 is a color photograph of a 12 yr old specimen of the parent tree.

DESCRIPTION OF THE VARIETY

Detailed Description

The mature tree height is about 12 m and the tree is tolerant to −12 C. (10 F.). The height, canopy diameter and trunk diameter of a 12 year old, non-irrigated tree in Kingsville was 5.6 m, 8.2 m and 0.25 m respectively. By using special site preparation techniques, none of the trees in the trial from which "Laurie" was selected, were irrigated at transplant or at any time during its life cycle. The spaces between the trees were cultivated and pre-emergence herbicides applied about every year. The tree would have undoubtedly grown faster had it not been adjacent to 3 similar sized trees in the 5 by 6 m spacing. A faster growing, *P. alba*(0618) that froze to the ground in 1983, later resprouted and was again severly damaged in 1989, had a basal diameter of 38 cm and a height of 7.3 m. Thus the new "Laurie" selection has slower height growth than other rapid growing *P. alba* types. Many nursery people believe the top growth of *P. alba* is too rapid, leading to considerably windthrow in windy wet weather. Thus the slower growth of "Laurie" should be an advantage. After 12 years growth the tree has not any suffered any apparent damage from wind or rain but one of the major scaffold branches in the upper canopy has split at the crotch. The tree canopy had a broad hemispherical shape that from a distance had few discernable main branches 2 m above the ground. The tree had no central stem above 2 m, but had several co-dominant main branches with crotch angles of about 60–80 degrees. The tips of the terminal branches had a weeping nature. The terminal branches had about 14 pair of leaves in a distance of 45 cm. Thus the internode length was about 3.2 cm. The bark on the main trunk was strongly fissured with openings about 12 mm wide and 20 cm long being common.

As of 1994, the "Laurie" tree had not been grown under luxury water consumption. When grown in 20 liter pots on a drip system, the trees have considerably greater basal diameter per unit of height than other *Prosopis alba.* For example, rooted cuttings of "Laurie" trees, that were planted in October were only 1.25 m tall by the following August, but they had basal collar diameters ranging from 15 to 21 mm with a mean of about 18 mm. A typical collar diameter for other *P. alba* types of the same height would be 10 mm. In the summer of 1994, 0.3 m tall rooted cuttings grew to a height of 1.2 m in a 20 liter pot under drip irrigation in 4 months.

Leaves: Individual pinnae are about 11–13 cm long. Typically there are 4 pairs of pinnae per leaf. The distance between the attachment of the pinnae to the rachis is about 16 mm. There are about 52 pairs of leaflets per pinnae spaced about 1 mm apart on the rachis. Leaflets are about 2 mm wide and 7–8 mm long. The leaf color of The Royal Horticultural Society Color Chart ranges from 137 A Green Group for the mature leaves to 137 C Green Group from the immature leaves. This information on foliage color is presented since there is considerable confusion among Arizona nurseries as to the species and colors of the "Argentine" and "Chilean" mesquites.

The immature leaves and stems are pubescent. When tender greenhouse grown leaves are viewed under a dissecting microscope on an Improved Neubauer Counting Background, the pubescent hairs are found to range from 0.05 mm to 0.10 mm in length. When the young stems are viewed in profile, the pubescent hairs are closer than 0.05 mm along the length of the stems. No pubescence of any kind was observed under the same magnification for *Prosopis alba* B2V50 and two other non-cold hardy *Prosopis alba* from Texas A&M University field collection. A *Prosopis velutina* accession had about the same density of pubescent hairs, but they were about 0.4 mm along. Two *Prosopis velutina* accessions, 0020 and 0032 were planted in the same California field trial as the parent *P. alba* 0039 of *P. alba* 0591 and could have hybridized with the parent 0039 giving rise to *P. alba*×*P. velutina* hybrid seeds with increased cold hardiness.

Thorns: Essentially thornless but at certain times of the year, a small percentage of the branches may have thorns less than 4 mm long.

Flowering habits: The colors and shape of the perfect, self-incompatible flowers are not deemed to be particularly distinguishing for this selection. The flowers do not have an odor. The sickle shaped pods are about 14–16 mm wide, 4–6 mm thick. The color of the pods immediately after they fall to the ground is Greyed-yellow 162 Group B according to The Royal Horticultural Society of London Colour Chart. The pods are curved in two dimensions with the straight-line distance of the pods tip to tip varying from 8 to 11 cm. The pods are sweet to the taste with very little astringent taste. The seeds are arranged perpendicular to the main axis of the pods. The "Laurie" seeds are 4.5 mm wide and 7 mm long. The weight of 10 "Laurie" seeds was 498 mg, in contact to 450 mg for 10 seeds of *P. alba* 0166 and 540 mg for 10 seeds of *P. velutina* 0454(0020). The Laurie seeds are slightly lighter in color i.e. Greyed Orange Group 165 B as opposed to the *P. velutina* 0454(0020) which are Greyed Orange Group 165A or *Prosopis alba* 0166 Greyed Orange Group 165A to 166A. In Kingsville, Tex. the pods ripen and fall to the ground from early June through late August. Depiste the fact that the "Laurie" tree and its 100 siblings are located only several hundred meters on one side by a university of 6,000 students and on the other side by a major subdivision, deer can nearly always located in the plots due to the sweet pods and the favorable habitat.

Bark color: The bark color of the mature trees depends on where the tree is grown. In the high humidity area of southern Texas where lichens and other epiphytes predominate, the bark of 12 year old trees have a grey color(Royal Society of Horticulture Black 202 D). In the greenhouse, where epiphytes do not occur, the bark color of 5–8 cm diameter stems is intermediate between the Greyed Orange Group 177A and the Greyed Orange Group 165A.

I claim:

1. A new and distinct variety of South American Mesquite substantially as illustrated and described, characterized by its cold hardiness to −12 C. (10 F.), its lack of spines, its resistance to stem cankers caused by *Lasiodiplodia theobromae* and *Pestalotiopsis guepinii,* and its greater girth to height ratio than clone *P. alba* B2V50 that provides trees with less of a tendency to lean in the wind.

* * * * *

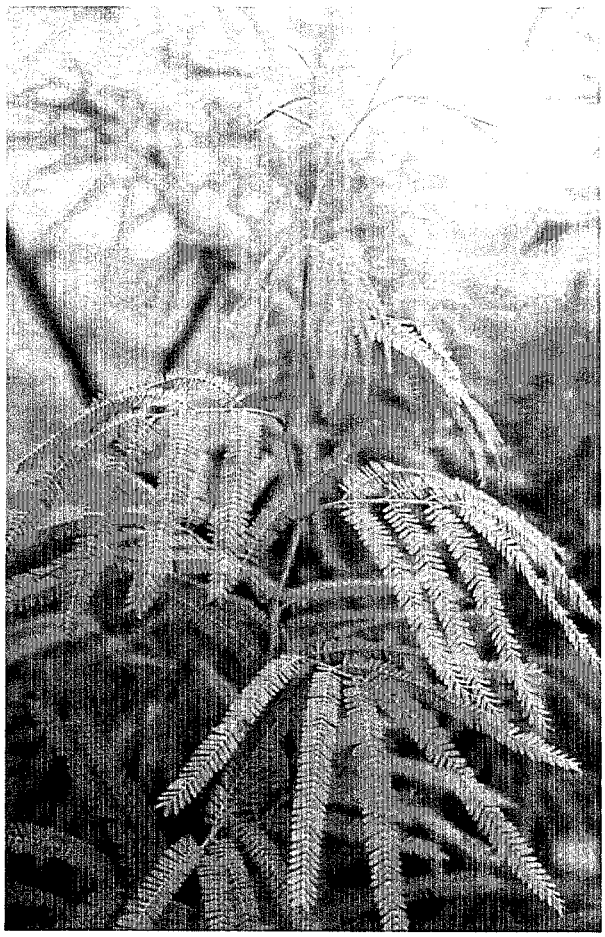

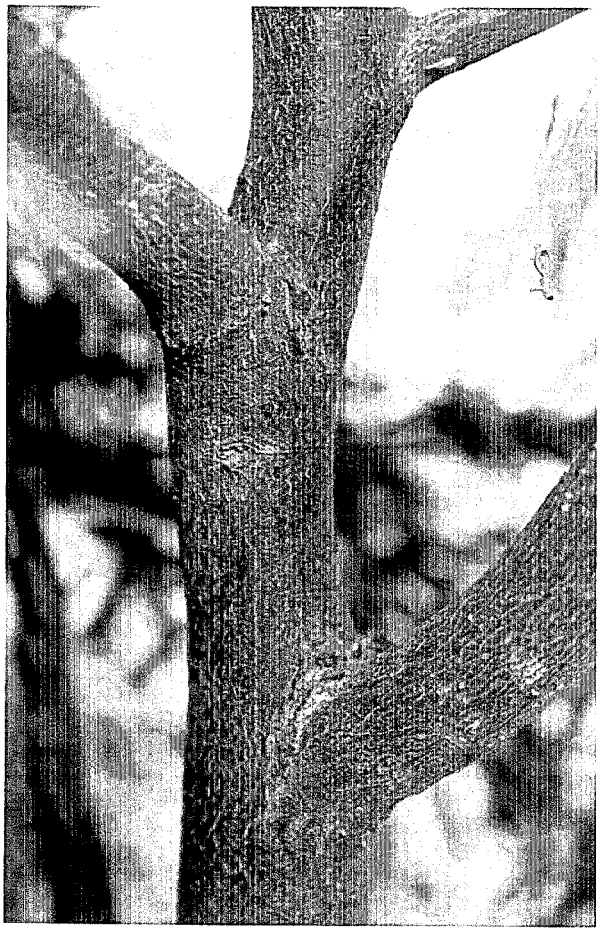

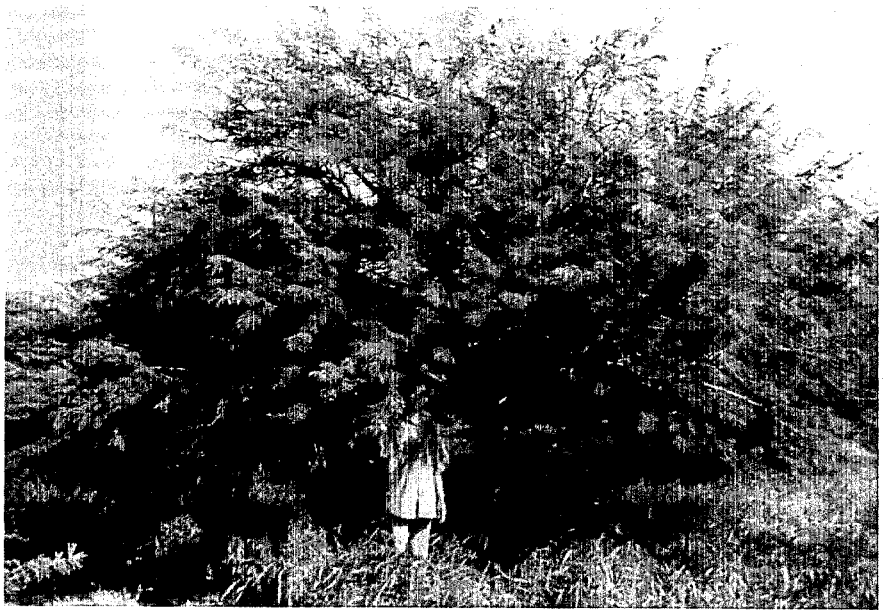

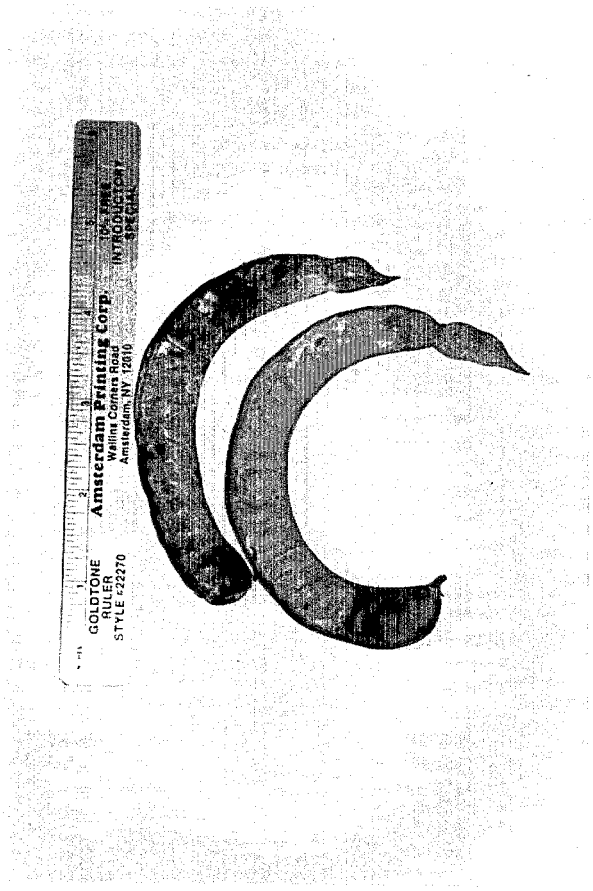
GOLDTONE
RULER
STYLE #22270
Amsterdam Printing Corp.
Walling Corners Road
Amsterdam, NY 12010